United States Patent [19]

Mandl

[11] 4,252,126
[45] Feb. 24, 1981

[54] TRANSDUCER DOME

[75] Inventor: Joseph P. Mandl, Lancaster, Ohio

[73] Assignee: Medex Inc., Hilliard, Ohio

[21] Appl. No.: 61,183

[22] Filed: Jul. 27, 1979

[51] Int. Cl.³ .............................................. A61B 5/02
[52] U.S. Cl. ................................... 128/673; 128/675;
128/748; 73/706; 73/756
[58] Field of Search ...................... 128/673, 675, 748;
73/706, 756

[56] References Cited

U.S. PATENT DOCUMENTS

| 3,565,056 | 2/1971 | Statham | 128/675 X |
| 3,631,850 | 1/1972 | Levasseur | 128/675 |
| 3,818,765 | 6/1974 | Eriksen | 128/675 X |
| 3,865,100 | 2/1975 | Kanai et al. | 128/675 |
| 4,063,553 | 12/1977 | Karsh | 128/214 F |
| 4,072,056 | 2/1978 | Lee | 73/706 |
| 4,170,224 | 10/1979 | Garrett et al. | 128/748 |

Primary Examiner—Kyle L. Howell
Attorney, Agent, or Firm—Wood, Herron & Evans

[57] ABSTRACT

A transducer dome for isolating a transducer from the liquid which actuates it. The transducer dome has a hemispherical or conical portion containing a single inlet and a threaded portion for connection to a transducer. The inlet is isolated from the transducer by a diaphragm formed from a hydrophobic bacterial filter, which allows venting of air during priming.

4 Claims, 3 Drawing Figures

U.S. Patent  Feb. 24, 1981  4,252,126
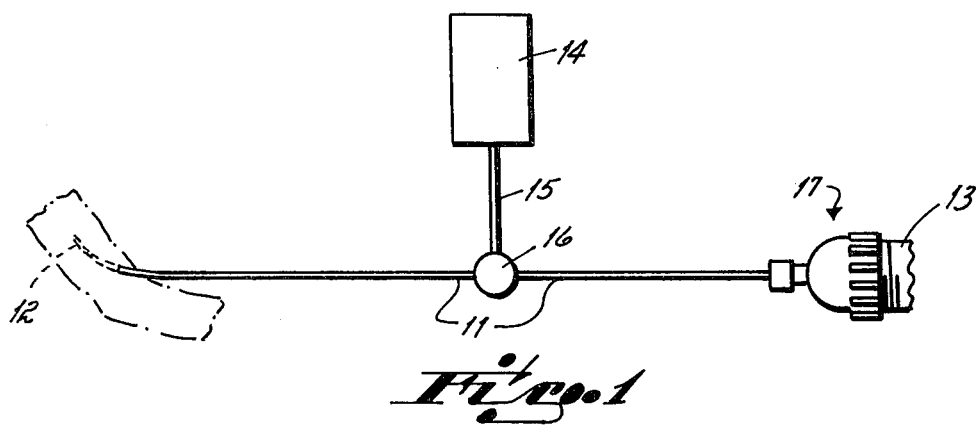
*Fig. 1*
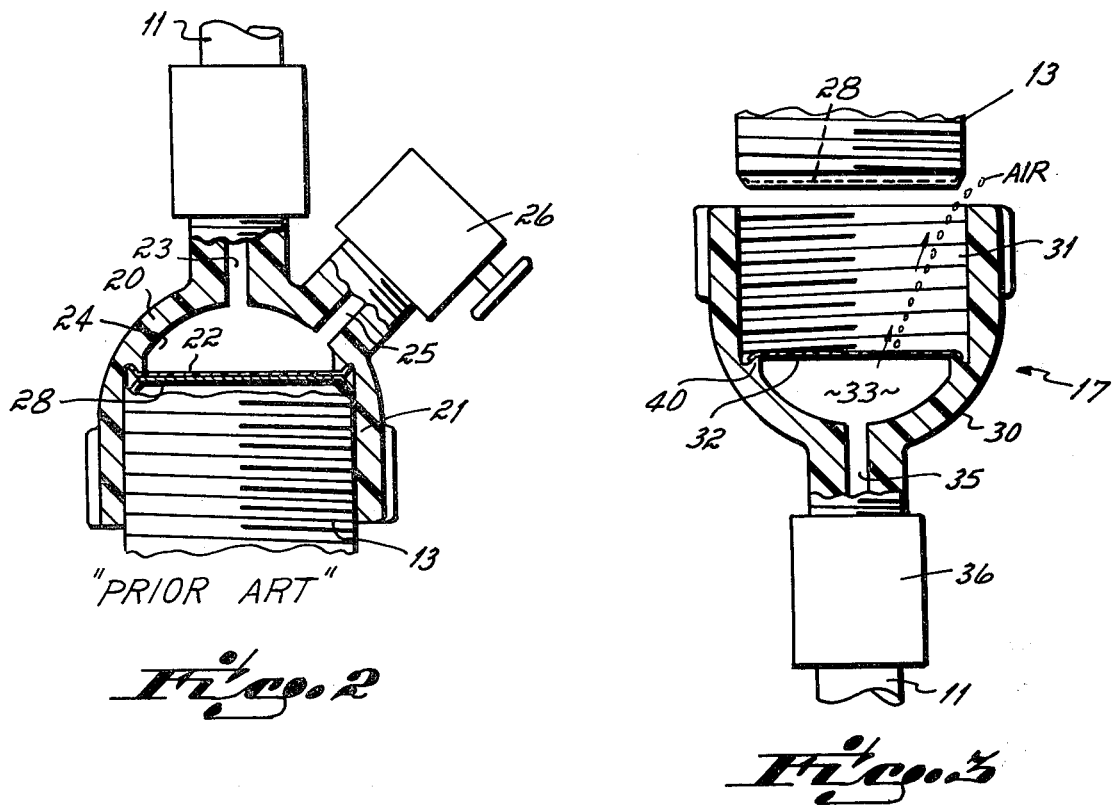
"PRIOR ART"
*Fig. 2*   *Fig. 3*

TRANSDUCER DOME

This invention relates to a transducer dome for use in a catheter system by monitoring blood pressure.

The monitoring system is of the type disclosed in application Ser. No. 953,036, filed Oct. 20, 1978. In that system a catheter is placed in the blood vessel of a patient and is connected by a tube to a transducer which is in turn connected to a monitor which graphically records signals from the patient. The tube is filled with a sterile physiological solution and pulses from the patient are transmitted via the virtually incompressible liquid to the transducer diaphragm. All the signals impinging on the transducer diaphragm are converted to electrical pulses which are recorded by the monitoring apparatus.

The transducer must be sterilized after each use or, alternatively, must be maintained isolated from the solution entering the patient's body. Since the transducer is an expensive instrument and since the sterilization process tends to substantially shorten the life of the transducer, it is economically preferable to isolate the transducer from the sterile physiological solution.

The device by which the transducer is isolated from the liquid in the tube is a transducer dome. The transducer dome which has been used heretofore consists of a hemisphere and an integral threaded connection, the hemisphere and the connection being separated by a flexible plastic diaphragm. The hemisphere has an inlet through which a connection to the tube containing the sterile physiological solution is made. The dome is mounted on the transducer by means of the threaded connection. When the dome is threaded snugly onto the transducer, the transducer diaphragm and the transducer dome snugly contact each other. Pulses which are transmitted from the patient through the liquid impinge upon the dome diaphragm and are directly transmitted to the transducer diaphragm which is in contact with it. Thus, there is a mechanical communication between the pulses transmitted through the liquid and the transducer diaphragm, but the liquid and the transducer diaphragm are maintained insulated or isolated from each other by the dome diaphragm.

The transducer dome is provided with a second passageway in addition to the inlet for the purpose of permitting the escape of all entrapped air before the system is used. Obviously, the entrapped air would adversely affect the frequency response of the system in view of the compressibility of the air. In other words, pulses would tend to be absorbed in the compressing of the air rather than impinging fully on the dome diaphragm. Therefore, the air must be bled from the system through the second outlet. That second outlet is normally provided with a plug or a stopcock so that it can be opened for escape of air and closed off after the air has been bled from the system.

The transducer dome as thus described is expensive because of the second passageway and associated stopcock, but more importantly, it is a difficult undertaking for the attending nurse or technician to bleed a dome completely free of air. Because of the configuration of the dome, air bubbles tend to get trapped in the dome and the dome must be twisted, turned, banged, and shaken in order to get the bubbles to move completely to the outlet passageway.

It has been an objective of the present invention to simplify the transducer dome structure so that it can be manufactured less expensively.

It has been another objective of the invention to simplify the method of getting fluid into the transducer dome and getting air out of the transducer dome.

These objectives of the invention are attained by providing a transducer dome generally of the type described having a hemisphere or conical chamber and a threaded connection. The transducer dome of the present invention is distinguished from the prior art in the elimination of the second outlet passageway and in the substitution for the known impervious diaphragm of a hydrophobic bacterial filter material. The hydrophobic diaphragm material repels liquid and passes air. Its liquid repelling characteristics are such that liquid does not wick through the filter but remains totally isolated from the transducer diaphragm which is in contact with the other side of the filter.

Using the transducer dome of the present invention, the nurse or technician, in setting up the system, merely holds the threaded connection side of the dome in an upwardly-facing attitude as she/he fills the tube and the hemisphere or conical chamber with liquid. The air in the dome simply passes upwardly through the diaphragm to the atmosphere until the dome is filled with liquid and all air has escaped. No manipulation on the part of the nurse or technician is required as long as the transducer side of the dome is facing upwardly and the inlet is facing downwardly.

The several features and objectives of the invention will become more readily apparent from the following detailed description taken in conjunction with the accompanying drawings in which:

FIG. 1 is a diagrammatic view of the monitoring system;

FIG. 2 is an elevated view partly in section of the prior art transducer dome; and FIG. 3 is a cross-sectional view through the transducer dome of the present invention.

The system with which the present invention is used includes a main tube 11 having a catheter 12 at one end which is insertable into the blood vessel of the patient and a transducer 13 at the other end of the main tube. A physiological solution is fed into the main tube from a supply 14 passing through a tube 15 into a constant flush valve assembly 16 connected to the main tube. The constant flush valve flush system might be of the type shown in application Ser. No. 953,036 or application Ser. No. 061,305, filed July 27, 1979.

The solution in the main tube 11 is connected to the transducer 13 by means of a transducer dome 17, the transducer 13 being threaded into the transducer dome.

A prior art dome is shown in FIG. 2. The dome consists of a hemisphere 20 integral with a threaded connection 21. The hemisphere 20 and the threaded connection 21 are isolated from each other by a flexible impervious plastic diaphragm 22. The dome has an inlet passageway 23 by which the physiological solution is introduced into a cavity 24 defined by the dome and the diaphragm. The hemisphere also has an outlet passageway 25 normally connected to a stopcock 26 by which air is bled from the dome when the physiological solution is introduced. The threaded connection 21 receives the transducer 13 in such a way that its diaphragm 28 is in contact with the impervious diaphragm 22. It can be seen that when a physiological solution is introduced through the inlet 23 that air entrapped in the dome in the form of bubbles can only be caused to escape through the passageway 25 if the dome can be maneuvered in such a way that the bubbles move to the passageway.

The transducer dome of the present invention is shown in FIG. 3. There, a hemisphere or conical chamber 30 is integral with a threaded connection 31. A diaphragm 32 isolates the cavity 33 created by the hemisphere or conical chamber 30 from the threaded connection. The diaphragm 32 is a hydrophobic bacterial filter which repels liquid and passes air. The material has 0.2 micron pore size and is manufactured by Gilman Scientific Company of Ann Arbor, Mich. under the trademark ACROPOR. The dome has a single inlet passageway 35. The passageway 35 is preferably threaded and has a connector nut 36 by which a secure connection can be made to a flanged fitting at the end of the main tube 11. The transducer 13 is connected to the transducer dome by means of the threaded connection 31 so that the transducer diaphragm 28 is in intimate mechanical contact with the dome diaphragm 32.

The diaphragm 32 is either welded to a shoulder 40 in the dome in the manner that plastic diaphragms 22 have been mounted in the transducer dome or, alternatively, the dome can be made in two parts, namely, the hemisphere and the threaded connection, and thereafter, with the diaphragm sandwiched between the two parts, the parts can be welded together to form the integral dome with the diaphragm isolating the hemisphere from the threaded connection.

In the operation of the invention, with the transducer disconnected from the transducer dome, the main tube 11 is filled with the physiological solution while the transducer dome is held with the inlet 35 pointing down and the threaded connection 31 facing up. As the liquid fills the tube and flows into the cavity 33, all of the air in the cavity will be expelled through the pores in the diaphragm 32. No manipulation of the dome is required since the air will have no difficulty finding its way to the surface of the diaphragm 32 as long as the threaded connection 31 is facing generally in an upward direction.

After all of the air has been expelled, the transducer is threaded into the dome so that its diaphragm is in intimate mechanical contact with the dome diaphragm 32. The material, as well as being hydrophobic, is a bacterial filter which will not permit bacteria from the transducer to pass to the liquid. Further being hydrophobic, the filter will not permit the liquid to wick through the diaphragm and thus make contact with the transducer.

It can be seen that the transducer dome is less expensive than the prior art dome in the elimination of the second outlet and the elimination of the stopcock which is necessary to control the flow of fluid in the dome. It can also be seen that the transducer of the present invention is much more convenient to operate in that there is no problem in elimination of bubbles from the dome as it is being filled with the saline solution.

Having described my invention, I claim:

1. A transducer dome comprising,
    a housing,
    an inlet connection for liquid,
    means for connecting a transducer to said housing,
    and a diaphragm mounted across said housing between said inlet and said connecting means,
    said diaphragm being a hydrophobic bacterial filter which repels liquid and permits gas to pass through the filter.

2. A transducer dome as in claim 1 wherein said diaphragm has a 0.2 micron pore size.

3. A transducer dome comprising,
    a dome,
    an inlet in said dome,
    an internally-threaded extension of said dome adapted to receive a transducer,
    a diaphragm disposed across said dome and isolating said inlet from said threaded extension,
    said diaphragm consisting of a hydrophobic bacterial filter which repels liquid and permits air to pass through it.

4. The method of making a connection to a transducer for monitoring pulses transmitted through a solution using a transducer dome having a single inlet on one side, a transducer connection on the other side and a hydrophobic filter separating said inlet and said connection, comprising the steps of:
    connecting said inlet to a tube to be connected to a catheter,
    holding said inlet in a downward attitude and said filter in an upwardly-facing attitude while introducing a liquid into said main tube,
    continuing to introduce liquid into said main tube until said liquid fills the space between said inlet and said filter, the air escaping through said filter to atmosphere,
    and connecting said transducer to said dome with the transducer diaphragm contacting said filter.

* * * * *